United States Patent
Silliman et al.

(10) Patent No.: US 8,745,888 B2
(45) Date of Patent: Jun. 10, 2014

(54) ALIGNMENT TOOL FOR USE WITH A WIND TURBINE INSPECTION SYSTEM AND METHODS OF ASSEMBLING SAME

(75) Inventors: George Rowan Silliman, Rensselaer, NY (US); James Leo Gauthier, Spring, TX (US); Andre Jonathan Filiatrault, Spring, TX (US); Richard John Bever, Delanson, NY (US)

(73) Assignee: General Electric Company, Schenectady, NY (US)

( * ) Notice: Subject to any disclaimer, the term of this patent is extended or adjusted under 35 U.S.C. 154(b) by 404 days.

(21) Appl. No.: 13/154,811

(22) Filed: Jun. 7, 2011

(65) Prior Publication Data
US 2012/0024068 A1    Feb. 2, 2012

(51) Int. Cl.
*G01D 21/00* (2006.01)
*G01N 29/00* (2006.01)

(52) U.S. Cl.
USPC .............................................. 33/645; 73/632

(58) Field of Classification Search
USPC ...................................... 73/598, 632; 33/645
See application file for complete search history.

(56) References Cited

U.S. PATENT DOCUMENTS

| | | | |
|---|---|---|---|
| 4,531,663 A | 7/1985 | Kajiyama et al. | |
| 4,677,916 A * | 7/1987 | Dodd | 104/118 |
| 6,993,971 B2 | 2/2006 | Bossi et al. | |
| 2007/0058854 A1* | 3/2007 | Caskey et al. | 382/152 |
| 2008/0141778 A1* | 6/2008 | Bosselmann et al. | 73/633 |
| 2010/0218609 A1 | 9/2010 | Reed et al. | |
| 2011/0008168 A1 | 1/2011 | Fuglsang-Petersen et al. | |

OTHER PUBLICATIONS

Search Report issued in connection with EP Application No. 12170275.7, Sep. 13, 2012.

* cited by examiner

*Primary Examiner* — Hezron E Williams
*Assistant Examiner* — David Z Huang
(74) *Attorney, Agent, or Firm* — James McGinness; Armstrong Teasdale LLP

(57) ABSTRACT

An alignment tool for use in inspecting a ring gear of a gearbox. The ring gear includes an outer surface and a plurality of gear teeth extending radially inwardly from the outer surface. The alignment tool includes a support member that extends between a leading edge and a trailing edge. The support member is removably mountable to the ring gear outer surface such that the leading edge is oriented substantially parallel to a forward surface of the ring gear. A guide member extends outwardly from the support member. The guide member includes a guide edge that is oriented with respect to a centerline of a gear tooth.

18 Claims, 6 Drawing Sheets

ALIGNMENT TOOL FOR USE WITH A WIND TURBINE INSPECTION SYSTEM AND METHODS OF ASSEMBLING SAME

BACKGROUND OF THE INVENTION

The subject matter described herein relates generally to wind turbines and, more particularly, to an alignment tool for use with a wind turbine inspection tool.

At least some known wind turbine towers include a nacelle fixed atop a tower. The nacelle includes a rotor assembly coupled to a generator through a shaft. In known rotor assemblies, a plurality of blades extend from a rotor. The blades are oriented such that wind passing over the blades turns the rotor and rotates the shaft, thereby driving the generator to generate electricity.

Because many known wind turbines provide electrical power to utility grids, at least some wind turbines have larger components (e.g., rotors in excess of thirty-meters in diameter) that facilitate supplying greater quantities of electrical power. However, the larger components are often subjected to increased loads (e.g., asymmetric loads) that result from wind shears, yaw misalignment, and/or turbulence, and the increased loads have been known to contribute to significant fatigue cycles on the gearbox assembly and/or other components of the wind turbine.

At least some known wind turbines include an electric generator and a gearbox each positioned within the nacelle. The electric generator is coupled to the gearbox with a high speed shaft. At least some known gearbox assemblies include a ring gear assembly that engages a gear assembly to facilitate transferring rotational energy from a low speed rotor shaft to a high speed shaft that rotatably drives the generator to facilitate producing electrical power. Over time, the ring gear assembly may become worn. As the ring gear assembly becomes worn, the gearbox assembly becomes less effective in transferring rotational energy to the generator. In at least some known wind turbines, visual inspection of the interior of the gearbox is used to find large defects such as missing sections of the gear teeth, however, the distance between the gearbox assembly and the generator is such that access to the ring gear to perform the interior inspection is limited. As such, visual inspection of the interior of the ring gear is time-consuming and causes increased downtime and expense to perform the inspection.

Accordingly, it is desirable to provide a system and method capable of monitoring the gearbox assembly that does not require visual inspection of the interior of the ring gear assembly.

BRIEF DESCRIPTION OF THE INVENTION

In one aspect, an alignment tool for use in inspecting a ring gear of a gearbox is provided. The ring gear includes an outer surface and a plurality of gear teeth extending radially inwardly from the outer surface. The alignment tool includes a support member that extends between a leading edge and a trailing edge. The support member is removably mountable to the ring gear outer surface such that the leading edge is oriented substantially parallel to a forward surface of the ring gear. A guide member extends outwardly from the support member. The guide member includes a guide edge that is oriented with respect to a centerline of a gear tooth.

In another aspect, an inspection system for inspecting a condition of a ring gear of a gearbox is provided. The ring gear includes an outer surface and a plurality of gear teeth extending radially inwardly from the outer surface. The inspection system includes a monitoring device for monitoring a condition of the ring gear. A transducer is coupled to the monitoring device. The transducer is positioned adjacent the ring gear outer surface and is configured to generate a signal indicative of a defect defined within the ring gear. An alignment tool is removably coupled to the ring gear outer surface. The alignment tool includes a guide edge that is oriented substantially parallel to a centerline axis of a predefined ring gear tooth. The transducer contacts the guide edge and travels along the guide edge to scan along a length of the ring gear tooth.

In yet another aspect, a method of inspecting a gearbox including a ring gear having a plurality of gear teeth extending radially inwardly from an outer surface is provided. The method includes removably coupling an alignment tool to the ring gear. The alignment tool includes a support member extending between a leading edge and a trailing edge, and a guide member extending outwardly from the support member. The guide member includes a guide edge oriented obliquely to the leading edge. The alignment tool is positioned with respect to a first gear tooth such that the guide edge is oriented with respect to a centerline axis of the first ring gear tooth. A transducer is positioned adjacent the guide edge. A first signal that is indicative of the first ring gear tooth is transmitted from the transducer to a monitoring device.

DETAILED DESCRIPTION OF THE INVENTION

The embodiments described herein overcome at least some disadvantages of known wind turbines by providing a wind turbine inspection system that enables the ring gear assembly to be inspected without requiring an operator to visually inspect the interior of the ring gear. More specifically, the inspection system described herein includes a transducer that removably mounted to an outer surface of the gearbox and is configured to generate a signal that is indicative of a flaw within the gear teeth of the ring gear. In addition, the inspection system described herein includes an alignment tool that is removably mountable to the gearbox outer surface and aligned along a gear tooth centerline to enable a user to scan the transducer along a length of the gear tooth. By scanning the length of the gear tooth, the alignment tool facilitates providing an accurate scan of the ring gear and reduces the time and expense of inspecting the ring gear assembly.

Figure 1:
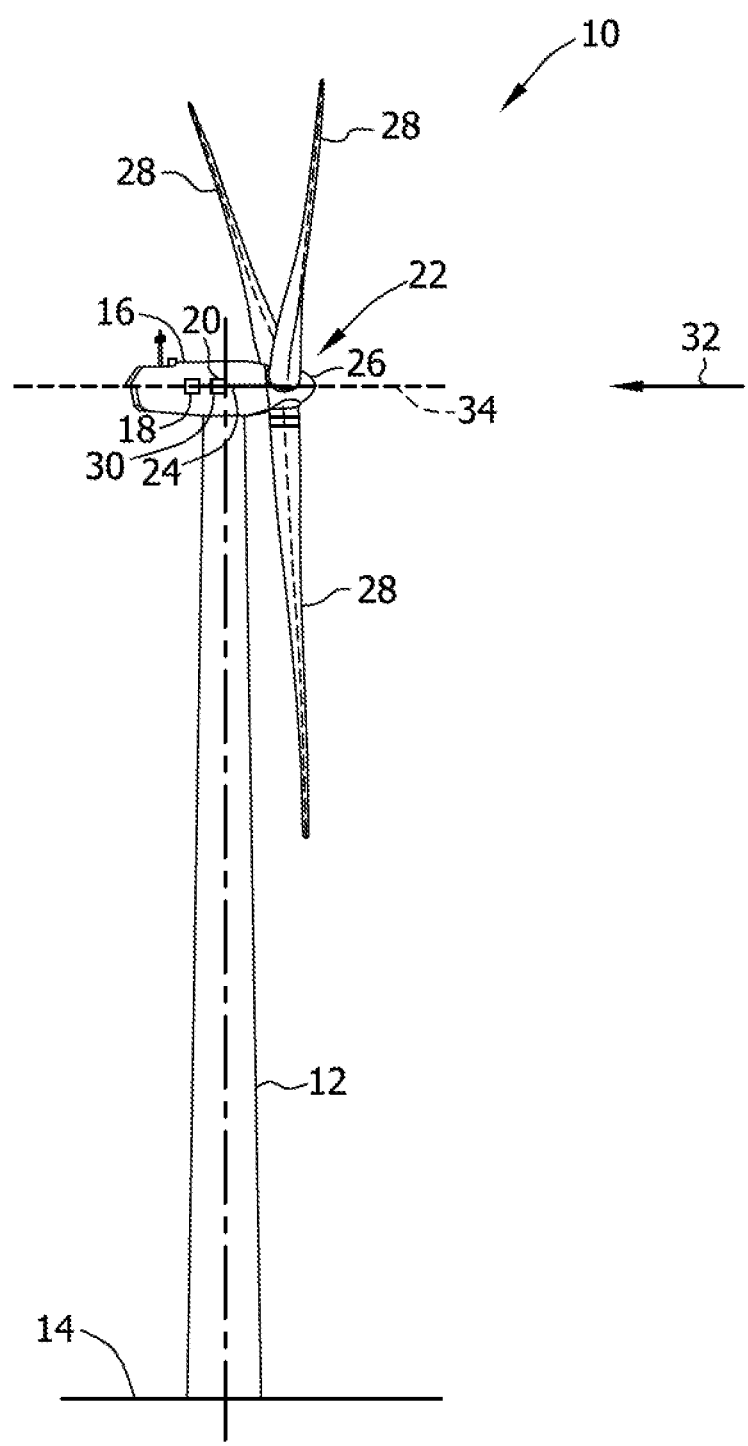
FIG. 1 is a perspective view of an exemplary wind turbine.

FIG. 1 is a perspective view of an exemplary wind turbine 10. In the exemplary embodiment, wind turbine 10 includes a tower 12 that extends from a supporting surface 14, a nacelle 16 that is mounted on tower 12, a generator 18 that is positioned within nacelle 16, and a gearbox 20 that is coupled to generator 18. A rotor 22 is rotatably coupled to gearbox 20 with a low speed shaft, i.e. a rotor shaft 24. Rotor 22 includes a rotatable hub 26 and at least one rotor blade 28 coupled to and extending outwardly from hub 26.

In the exemplary embodiment, rotor 22 includes three rotor blades 28. In an alternative embodiment, rotor 22 includes more or less than three rotor blades 28. Rotor blades 28 are spaced about hub 26 to facilitate rotating rotor 22 to enable kinetic energy to be transferred from the wind into usable mechanical energy, and subsequently, electrical energy. In the exemplary embodiment, each rotor blade 28 has a length ranging from about 30 meters (m) (99 feet (ft)) to about 120 m (394 ft). Alternatively, rotor blades 28 may have any suitable length that enables wind turbine 10 to function as described herein. For example, other non-limiting examples of rotor blade lengths include 10 m or less, 20 m, 37 m, or a length that is greater than 120 m.

In the exemplary embodiment, wind turbine 10 also includes a gearbox inspection system 30 for inspecting a condition of gearbox 20. Inspection system 30 is removably coupled to gearbox 20 for monitoring a condition of various components that are housed within gearbox 20 during operation of wind turbine 10.

During operation of wind turbine 10, as wind strikes rotor blades 28 from wind direction 32, rotor 22 is rotated about an axis of rotation 34 causing a rotation of rotor shaft 24 about axis 34. A rotation of rotor shaft 24 rotatably drives gearbox 20 that subsequently drives generator 18 to facilitate production of electrical power by generator 18. Over time, gearbox components may become worn. Gearbox inspection system 30 enables a user to monitor a condition of gearbox 20 without requiring a shutdown of wind turbine 10 and/or a removal of gearbox 20.

Figure 2:
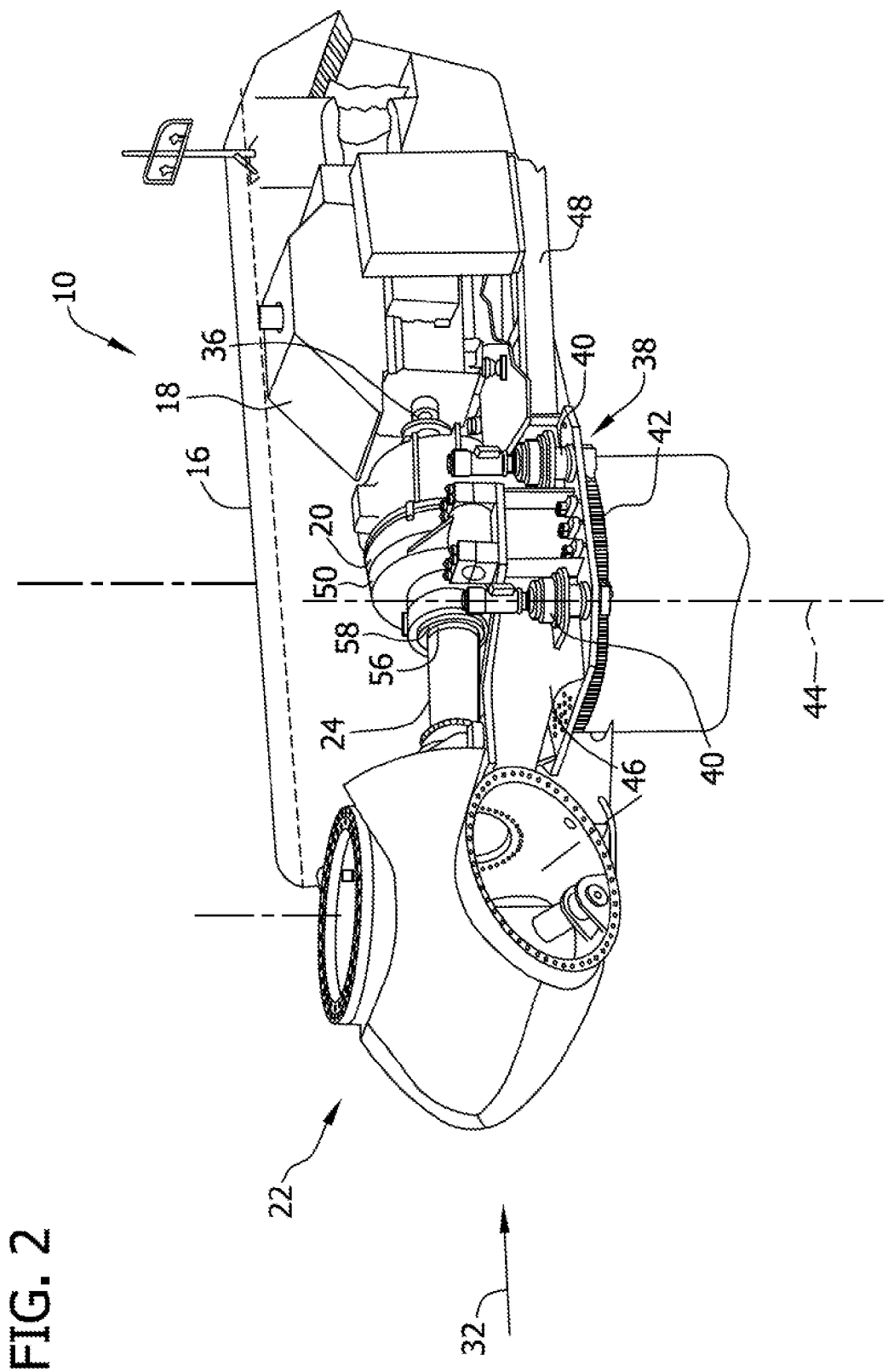
FIG. 2 is an enlarged perspective view of a portion of the wind turbine shown in FIG. 1.
Figure 3:
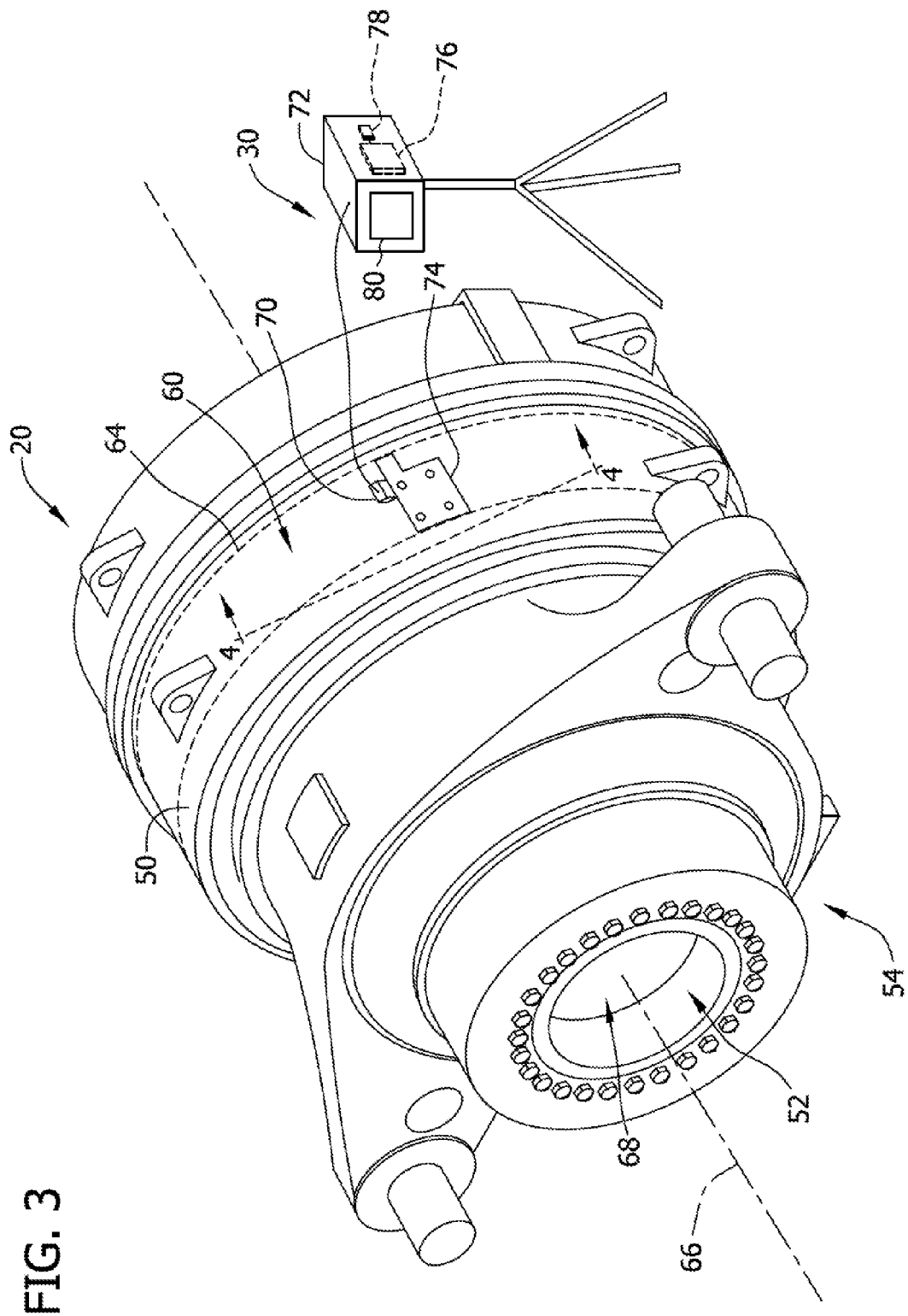
FIG. 3 is an enlarged perspective view of an exemplary gearbox suitable for use with the wind turbine shown in FIG. 1 including an exemplary gearbox inspection system.

FIG. 2 is an enlarged perspective view of a portion of wind turbine 10. FIG. 3 is a partial cross-sectional view of gearbox 20. In the exemplary embodiment, rotor shaft 24 is positioned within nacelle 16 and is coupled between rotor 22 and gearbox 20. A high speed shaft 36 is coupled between gearbox 20 and generator 18. In the exemplary embodiment, during operation of wind turbine 10, rotor shaft 24 rotates to drive gearbox 20 that subsequently drives high speed shaft 36. High speed shaft 36 rotatably drives generator 18 to facilitate production of electrical power by generator 18. Wind turbine 10 also includes a yaw system 38 including at least one yaw drive assembly 40 that is coupled to a yaw bearing 42. Yaw drive assembly 40 is configured to engage yaw bearing 42 to cause nacelle 16 and rotor 22 to rotate about yaw axis 44. Gearbox 20, rotor shaft 24, and yaw drive assembly 40 are each supported by a bedplate frame 46. Bedplate frame 46 is coupled to yaw bearing 42 to support bedplate frame 46 from tower 12. Generator 18 is supported by a generator frame 48 that is cantilevered from bedplate frame 46.

In the exemplary embodiment, gearbox 20 includes a gearbox housing 50 including an opening 52 that extends through a forward section 54 of housing 50. Gearbox 20 also includes an input shaft 56 that is positioned within opening 52 and is sized to receive rotor shaft 24. A shrink disk 58 is coupled to input shaft 56 to compress input shaft 56 about rotor shaft 24 to facilitate coupling input shaft 56 to rotor shaft 24 via a friction fit.

In addition, gearbox 20 includes a ring gear 60 and a planetary gear assembly (not shown). Ring gear 60 and the planetary gear assembly are each positioned within housing 50. The planetary gear assembly is rotatably coupled to ring gear 60, rotor shaft 24, and high speed shaft 36 such that a rotation of rotor shaft 24 causes a rotation of high speed shaft 36. Ring gear 60 includes a plurality of ring gear teeth 62 (shown in FIG. 4) that extend along an interior surface 64 (shown in phantom lines in FIG. 3) of ring gear 60. Interior surface 64 is oriented along a centerline axis 66 and defines a cavity 68 extending through ring gear 60. Ring gear teeth 62 are oriented to engage the planetary gear assembly to enable the planetary gear assembly to translate a rotation of rotor shaft 24 to a rotation of high speed shaft 36.

In the exemplary embodiment, gearbox inspection system 30 includes a transducer 70 that is removably mounted to gearbox housing 50 and is positioned with respect to ring gear 60 for monitoring a condition of ring gear teeth 62. Transducer 70 is communicatively coupled to a monitoring device 72 and is configured to generate a signal that is indicative of a condition of ring gear teeth 62, and to transmit the generated signal to monitoring device 72. Gearbox inspection system 30 also includes an alignment tool 74 that is removably coupled to housing 50 and is configured to position transducer 70 with respect to ring gear teeth 62.

In the exemplary embodiment, monitoring device 72 includes a processor 76 and a memory device 78. Processor 76 is coupled in communication with transducer 70, and includes any suitable programmable circuit which may include one or more systems and microcontrollers, microprocessors, reduced instruction set circuits (RISC), application specific integrated circuits (ASIC), programmable logic circuits (PLC), field programmable gate arrays (FPGA), and any other circuit capable of executing the functions described herein. The above examples are exemplary only, and thus are not intended to limit in any way the definition and/or meaning of the term "processor." Memory device 78 includes a computer readable medium, such as, without limitation, random access memory (RAM), flash memory, a hard disk drive, a solid state drive, a diskette, a flash drive, a compact disc, a digital video disc, and/or any suitable device that enables processor 76 to store, retrieve, and/or execute instructions and/or data.

Monitoring device 72 also includes a display 80 for displaying a graphical representation and/or notification to a user. Display 80 is coupled to processor 76 and may include a vacuum fluorescent display (VFD) and/or one or more light-emitting diodes (LED). Additionally or alternatively, display 80 may include, without limitation, a liquid crystal display (LCD), a cathode ray tube (CRT), a plasma display, and/or any suitable visual output device capable of displaying graphical data and/or text to a user. In the exemplary embodiment, a condition of gearbox 20, a condition of ring gear 60, a condition of ring gear teeth 62, and/or any other information may be displayed to a user on display 80. In addition, a graphical representation of gearbox 20, ring gear 60, and/or ring gear teeth 62, may be displayed to a user on display 80. Moreover, a graphical representation of defect within ring gear teeth 62 may be displayed to a user on display 80.

In the exemplary embodiment, transducer 70 includes an ultrasonic transducer that is configured to be scanned on the outside diameter of ring gear 60. Transducer 70 generates ultrasonic wave packets that are transmitted into ring gear 60. The wave packets propagate through the ring gear material. If defects are present in ring gear 60, such as, for example, a crack, a fracture, and/or a missing gear tooth, sound waves generated by transducer 70 will reflect from the defects. The reflected sound waves propagating from the defects will either follow a direct path back to transducer 70, or propagate to a surface of ring gear 60 where they will reflect and propagate towards transducer 70. Transducer 70 receives the reflected ultrasonic waves and converts the acoustic energy into electrical energy. The electrical signals indicative of the time-of-flight for the wave reflections, the amplitude of the reflected signals, and other characteristics of the reflections such as, for example, phase, frequency, and/or waveform shape, are transmitted from transducer 70 to monitoring device 72. Monitoring device 72 determines the size and location of the defect in the ring gear teeth 62 based, at least in part, on the received signals. In the exemplary embodiment, monitoring device 72 presents, on display 80, a graphical representation of ring gear teeth 62 and/or the sensed defect within ring gear teeth 62 based at least in part on the received signal.

In the exemplary embodiment, transducer 70 may be either a monolithic (single-crystal) operated at a 0-degree beam angle or mounted to a wedge to generate ultrasonic beams at angles other than 0 degrees. In addition, a phased-array transducer may also be used to generate a range of beam angles or multiple beam angles used for the ring gear evaluation. Alternatively, other transducers may be used, such as an electromagnetic acoustic transducer (EMAT), piezoelectric transducer, or monolithic piezoelectric transducer (MPT).

Figure 4:
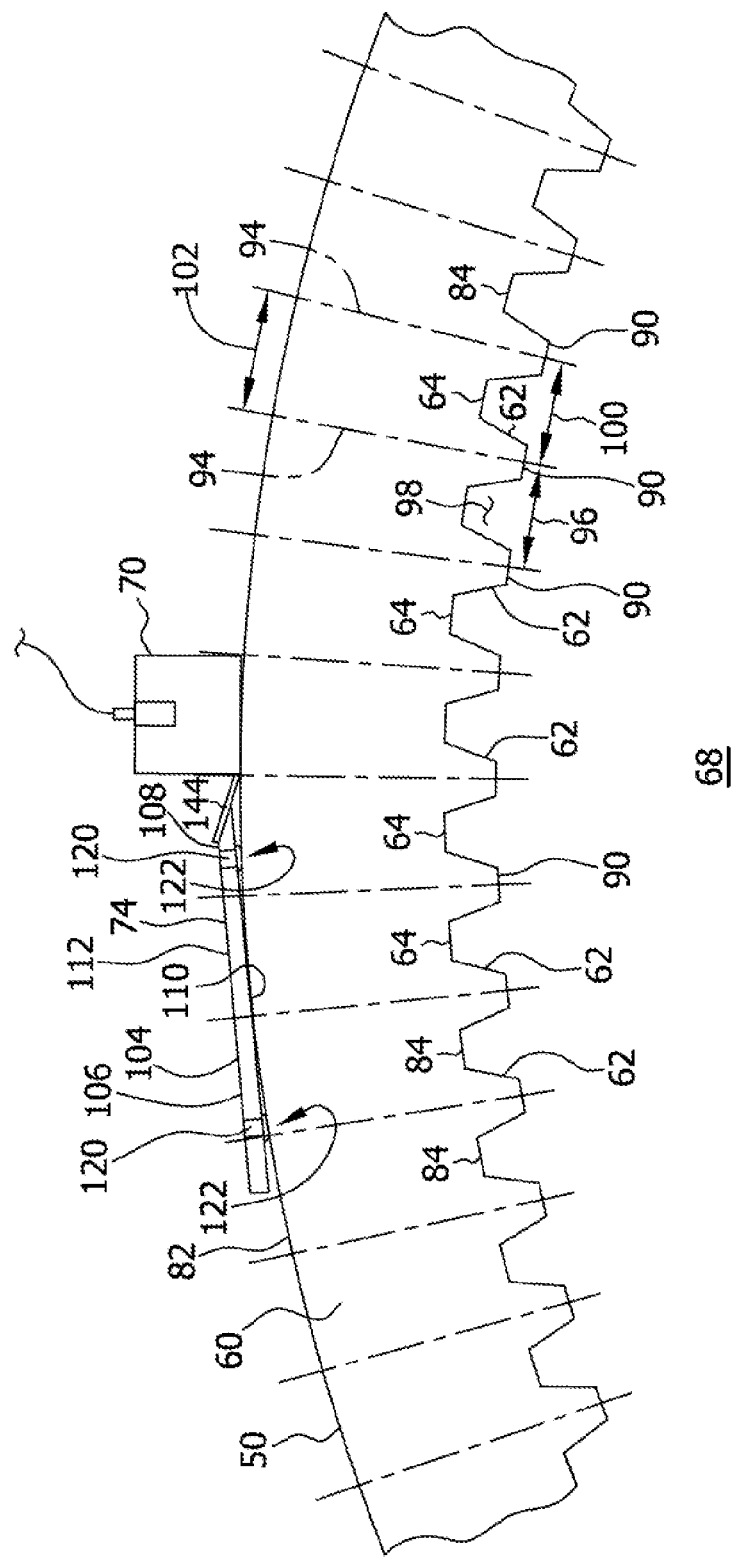
FIG. 4 is a cross-sectional view of a portion of the gearbox shown in FIG. 3 and taken along lines 4-4, including the gearbox inspection system shown in FIG. 3.
Figure 5:
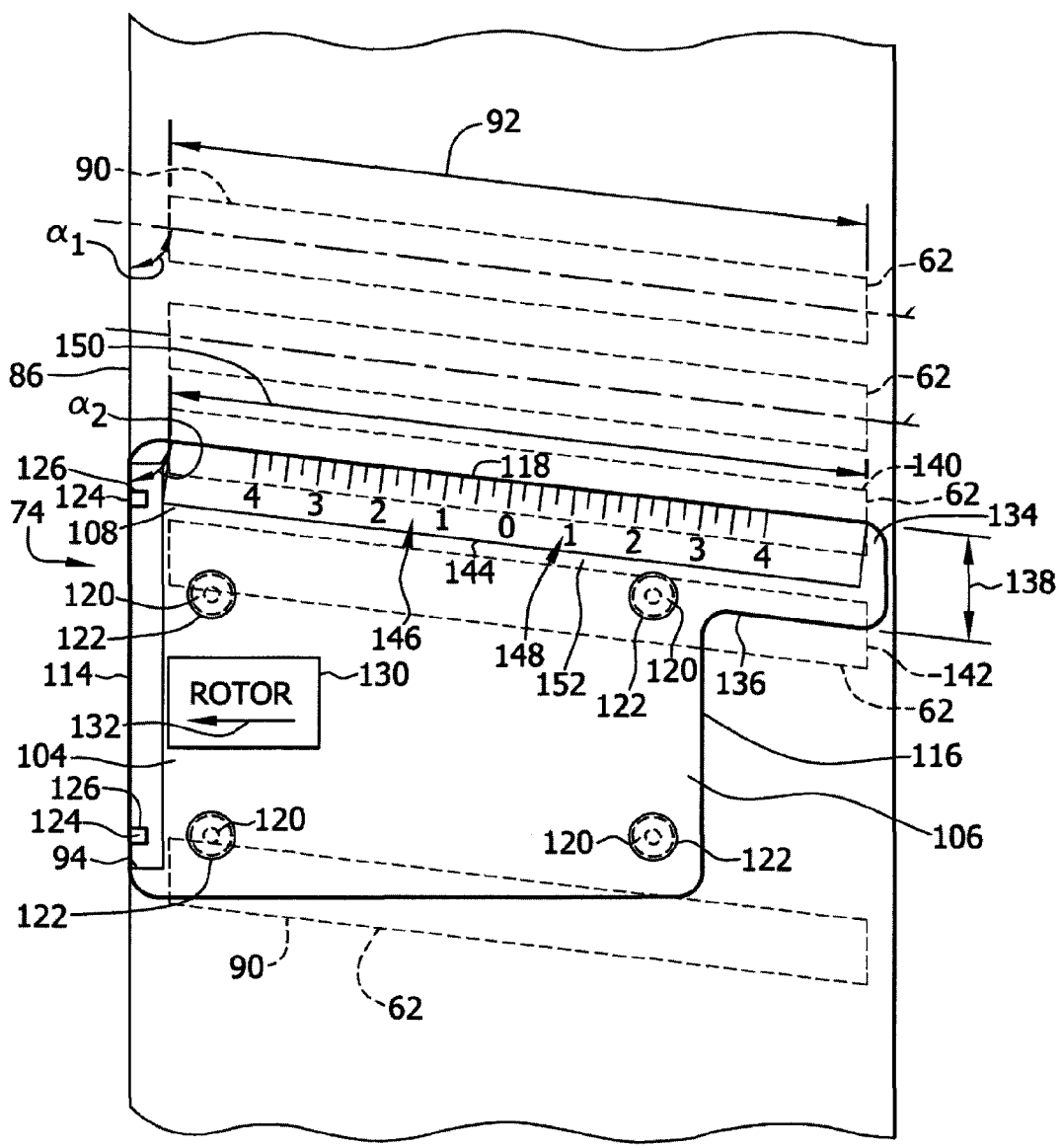
FIG. 5 is a perspective view of an exemplary alignment tool suitable for use with the gearbox inspection system show in FIG. 3.

FIG. 4 is a cross-sectional view of gearbox 20 taken along lines 4-4. FIG. 5 is a perspective view of alignment tool 74. Identical components shown in FIGS. 4-5 are labeled with the same reference numbers used in FIG. 3. In the exemplary embodiment, ring gear 60 includes an outer surface 82, such as an outer surface of housing 50, and an inner surface 84 that is coupled radially inwardly from outer surface 82. Inner surface 84 defines cavity 68. Ring gear 60 also extends axially between a forward surface 86 and an opposite aft surface 88. Each ring gear tooth 62 extends radially inwardly from inner surface 84 towards centerline axis 66, and extends axially between forward surface 86 and aft surface 88.

In the exemplary embodiment, ring gear teeth 62 are spaced circumferentially about inner surface 84. Each ring gear tooth 62 includes a top surface 90 that extends radially outwardly from inner surface 84 and is configured to engage the planetary gear assembly (not shown). Top surface 90 extends between forward surface 86 and aft surface 88 and has a length 92 that is measured between forward surface 86 and aft surface 88. Top surface 90 defines a centerline axis 94 of ring gear tooth 62. In the exemplary embodiment, each ring gear tooth 62 is oriented with respect to forward surface 86 such that a first oblique angle $\alpha_1$ is defined between gear tooth axis 94 and forward surface 86. Moreover, each ring gear tooth 62 is spaced a circumferential width 96 from an adjacent ring gear tooth 62 such that a gap 98 is defined between each adjacent ring gear teeth 62. Each ring gear tooth 62 is spaced such that a first width 100 is defined between adjacent gear tooth axes 94 at top surface 90, and a second width 102 is defined between adjacent axes 94 defined at ring gear outer surface 82 that is greater than first width 100.

In the exemplary embodiment, alignment tool 74 is removably coupled to ring gear outer surface 82 and is positionable with respect to a predefined ring gear tooth 62 to facilitate aligning transducer 70 between adjacent ring gear teeth 62. Alignment tool 74 is sized and shaped to enable transducer 70 to travel along outer surface 82 and be oriented with respect to gear tooth axis 94 to enable a user to scan transducer 70 along gear teeth length 92.

In the exemplary embodiment, alignment tool 74 includes an alignment plate 104 including a support member 106 and a guide member 108 integrally formed with support member 106. Alternatively, guide member 108 may be coupled to support member 106 with a weld and/or fastener. In the exemplary embodiment, support member 106 includes a radially inner surface 110 and a radially outer surface 112. Inner and outer surfaces 110 and 112 each extend between a leading edge 114 and an opposite trailing edge 116. Support member 106 is shaped such that leading edge 114 is oriented substantially parallel with ring gear forward surface 86. Guide member 108 extends outwardly from support member 106 and includes a guide edge 118 that extends from leading edge 114 towards trailing edge 116. Guide edge 118 is oriented obliquely with respect to leading edge 114 such that a second oblique angle $\alpha_2$ is defined between guide edge 118 and leading edge 114. In the exemplary embodiment, guide edge 118 is oriented substantially parallel to gear tooth axis 94 such that second angle $\alpha_2$ is approximately equal to first angle $\alpha_1$. Guide member 108 is sized and shaped to facilitate positioning transducer 70 with respect to gear tooth axis 94 during an inspection of ring gear 60.

In the exemplary embodiment, alignment tool 74 also includes a plurality of support magnets 120 that are coupled to support member 106 for magnetically coupling alignment tool 74 to ring gear outer surface 82. Support member 106 includes a plurality of openings 122 that are each sized and shaped to receive a support magnet 120 therethough. In the exemplary embodiment, each support magnet 120 extends outwardly from radially inner surface 110 to contact ring gear outer surface 82.

Alignment tool 74 also includes a plurality of alignment magnets 124 that are coupled to support member 106 and are positioned adjacent leading edge 114. Each alignment magnet 124 is spaced along leading edge 114 to facilitate orienting leading edge 114 substantially parallel to ring gear forward surface 86. In the exemplary embodiment, support member 106 includes a plurality of slots 126 that are each sized and shaped to receive an alignment magnet 124 therein. Alternatively, alignment magnets 124 may extend through support member 106 and extend outwardly from inner surface 110 to contact ring gear outer surface 82 near forward surface 86. In addition, alignment tool 74 also includes a label 130 that is attached to outer surface 112. Label 130 includes an arrow 132 indicating a location of rotor 22 with respect to ring gear 60 to assist a user in identifying forward surface 86 and an orientation of ring gear teeth 62.

In the exemplary embodiment, guide member 108 includes a spacing plate 134 that extends outwardly from support member trailing edge 116. Spacing plate 134 defines at least a portion of guide edge 118 and extends between guide edge 118 and an opposite rear edge 136. In the exemplary embodiment, spacing plate 134 has a width 138 measured between guide edge 118 and rear edge 136 that is approximately equal to ring gear teeth second width 102, such that guide edge 118 and rear edge 136 are oriented with respect to adjacent gear tooth axes 94. Moreover, rear edge 136 is oriented substantially parallel to guide edge 118 such that guide edge 118 is oriented with respect to a first gear tooth 140 and rear edge 136 is oriented with respect to a second gear tooth 142 that is adjacent first gear tooth 140. Rear edge 136 enables a user to mark a location of second gear tooth 142 such that the user may position guide edge 118 along gear tooth axis 94 of second gear tooth 142 after inspection of first gear tooth 140 has been completed.

Alignment tool 74 also includes a scaling plate 144 that is coupled to guide member 108 and oriented along guide edge 118. Scaling plate 144 includes a graduated scale 146 including graduated units of length 148 that enable a user to identify a location of transducer 70 along ring gear tooth 62. In the exemplary embodiment, scaling plate 144 includes a length 150 measured along guide edge 118 that is approximately equal to ring tooth length 92. Moreover, scaling plate 144 is oriented obliquely with respect to support member outer surface 112, and is oriented towards ring gear outer surface 82 to facilitate contacting transducer 70 and orient transducer 70 along gear tooth axis 94 during inspection. During inspection, when transducer 70 identifies a location of a defect within ring gear teeth, a user utilizes graduated scale 146 to identify the location of the defect along tooth length 92. In one embodiment, alignment tool 74 does not include scaling plate 144, and graduated scale 146 is defined along an outer surface 152 of guide member 108.

During inspection of ring gear 60, a user selectively positions transducer 70 along ring gear outer surface 82 and moves transducer 70 along outer surface 82 until a first gear tooth 140 is identified by transducer 70. The user then mounts alignment tool 74 onto outer surface 82 such that leading edge 114 is adjacent forward surface 86 and such that guide edge 118 is positioned adjacent transducer 70 and oriented with respect to gear tooth axis 94. The user moves transducer 70 along guide edge 118 to scan along length 92 of gear tooth 140. In addition, the user utilizes rear edge 136 to identify a location of a gear tooth axis 94 of an adjacent second gear tooth 142. After completion of the inspection of first gear tooth 140, the user repositions alignment tool 74 such that guide edge 118 is positioned with respect to second gear tooth axis 94. The user then positions transducer 70 adjacent guide edge 118 such that transducer 70 is aligned with respect to second gear tooth 142 to facilitate inspection of second gear tooth 142.

Figure 6:
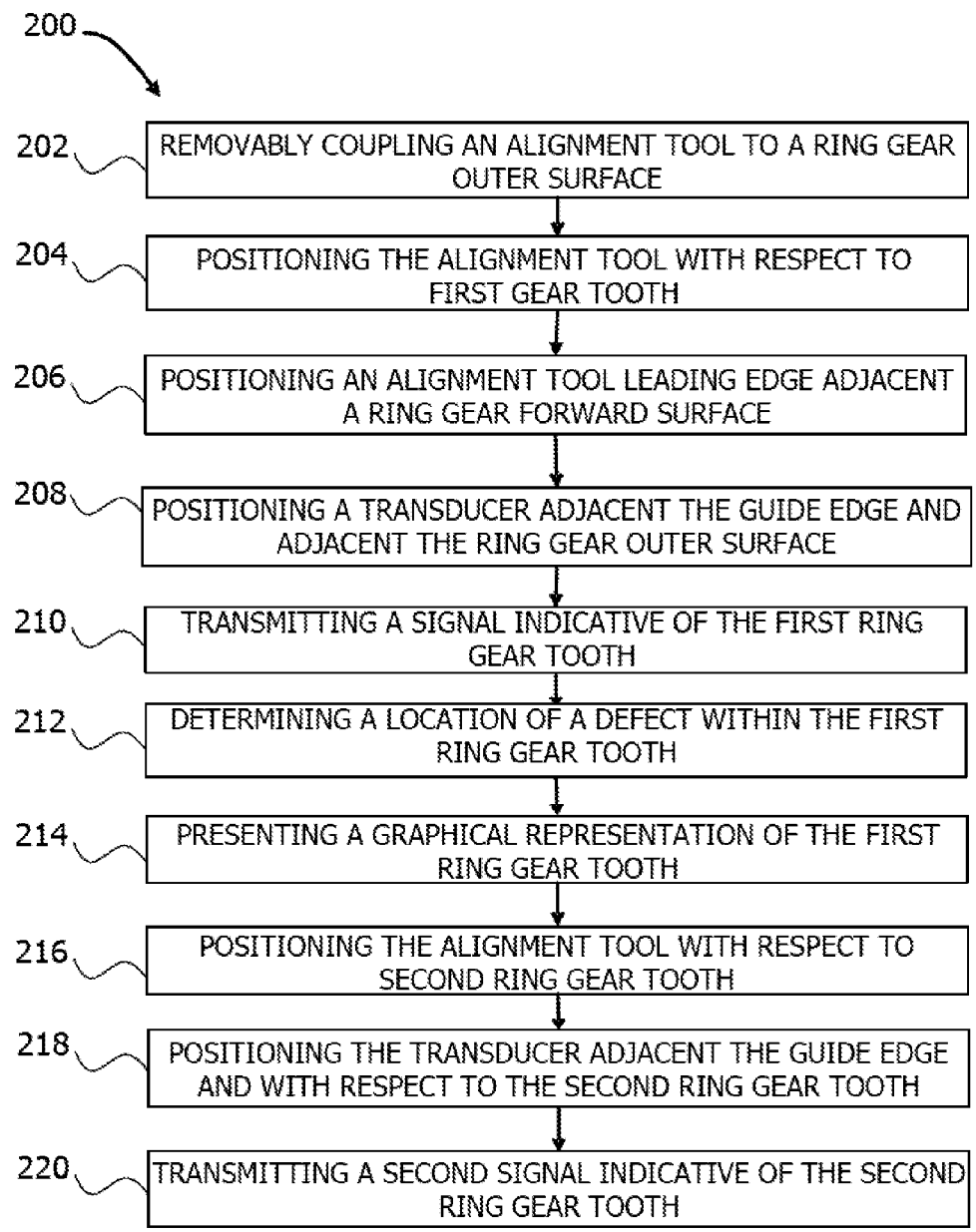
FIG. 6 is a flow diagram of an exemplary method of inspecting the gearbox shown in FIG. 3.

FIG. 6 is a flow chart of an exemplary method 200 of inspecting gearbox 20. In the exemplary embodiment, method 200 includes removably coupling 202 alignment tool 74 to ring gear outer surface 82, and positioning 204 alignment tool 74 with respect to first gear tooth 140 such that guide edge 118 is oriented with respect to centerline axis 94 of first ring gear tooth 140. In addition, method 200 includes positioning 206 alignment tool leading edge 114 adjacent ring gear forward surface 86. Moreover, method 200 includes positioning 208 transducer 70 adjacent guide edge 118 and adjacent ring gear outer surface 82, and transmitting 210, from transducer 70 to monitoring device 72, a signal indicative of first ring gear tooth 140. Monitoring device 72 determines 212 a location of a defect within first ring gear tooth 140 based at least in part on the received first signal. Moreover, monitoring device 72 presents 214 a graphical representation of first ring gear tooth 140 corresponding to the received first monitoring signal.

In the exemplary embodiment, method 200 also includes positioning 216 alignment tool 74 with respect to second ring gear tooth 142 such that guide edge 118 is oriented with respect to centerline axis 94 of second ring gear tooth 142. Transducer 70 is positioned 218 adjacent guide edge 118 such that transducer 70 is oriented with respect to second ring gear tooth 142, and transmits 220 a second signal indicative of second ring gear tooth 142.

According to aspects of the present invention, a method is provided for nondestructively inspecting ring gears that uses ultrasonic waves transmitted from the outer diameter of the ring gear. The ultrasonic waves can be used to evaluate the volume of the ring gear and the gear teeth located on the inner diameter. The method can use a combination of beam angles to interrogate the ring gear. The method may use fixed-angle monolithic ultrasonic probes and/or one or more phased-array probes operating at multiple angles generating a sector scan. The method can detect and identify defects in the volume of the ring gear including defects in the gear teeth.

The orientation and position of alignment tool 74 is selected to enable a user to scan transducer 70 across a full length of ring gear teeth 62 and to along gear tooth axis 94. In addition, the size and shape of alignment tool 74 is selected to facilitate a user marking a location of adjacent ring gear teeth 62 to enable the user to quickly reposition transducer 70 with respect to the adjacent ring gear teeth 62. By providing an alignment tool that enables a user to scan along a centerline of a ring gear tooth, and to mark an adjacent ring gear tooth to be scanned, the cost of inspecting the ring gear assembly is significantly reduced as compared to known inspection methods that require visual inspection of the interior of the gearbox assembly.

The above-described system and apparatus overcome at least some disadvantages of known wind turbines by providing a wind turbine inspection system that includes a transducer that removably mounted to an outer surface of the gearbox and is configured to generate a signal that is indicative of a flaw within the gear teeth of the ring gear. In addition, the inspection system described herein includes an alignment tool that is removable mountable to the gearbox outer surface and aligned along a gear tooth centerline to enable a user to scan the transducer along a length of the gear tooth. By providing an inspection system that includes an alignment tool that facilitates scanning the length of a gear tooth, the inspection system facilitates providing an accurate scan of the ring gear assembly and reduces the time and expense of inspecting the ring gear assembly. As such, the cost required to operate the wind turbine is significantly reduced.

Exemplary embodiments of an alignment tool for use with a wind turbine inspection system and methods of assembling an alignment tool are described above in detail. The systems and apparatus are not limited to the specific embodiments described herein, but rather, components of systems and/or apparatus may be utilized independently and separately from other components and/or steps described herein. For example, the systems may also be used in combination with other rotating systems, and are not limited to practice with only the gearbox assembly as described herein. Rather, the exemplary embodiment can be implemented and utilized in connection with many other rotating system applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An alignment tool for use in inspecting a ring gear of a gearbox, the ring gear including an outer surface and a plurality of gear teeth extending radially inwardly from the outer surface, said alignment tool comprising:

a support member extending between a leading edge and a trailing edge, said support member removably mountable to the ring gear outer surface such that said leading edge is oriented substantially parallel to a forward surface of the ring gear; and, a guide member extending outwardly from said support member, said guide member comprising a guide edge oriented with respect to a centerline of a gear tooth and oriented obliquely to and contacting the leading edge.

2. An alignment tool in accordance with claim 1, further comprising a plurality of support magnets coupled to said support member for removably coupling said alignment tool to the ring gear outer surface.

3. An alignment tool in accordance with claim 2, further comprising a plurality of alignment magnets positioned adjacent said leading edge, said plurality of alignment magnets spaced along said leading edge to facilitate orienting said leading edge substantially parallel to the ring gear forward surface.

4. An alignment tool in accordance with claim 1, wherein said guide member comprises a spacing plate extending outwardly from said support member trailing edge, said spacing plate extends between said guide edge and an opposite rear edge.

5. An alignment tool in accordance with claim 4, wherein said spacing plate includes a width measured between said guide edge and said rear edge that is approximately equal to a distance measured between adjacent ring gear teeth.

6. An alignment tool in accordance with claim 5, wherein said rear edge is oriented substantially parallel to said guide edge, said guide edge oriented with respect to a first gear tooth and said rear edge oriented with respect to an adjacent second gear tooth.

7. An alignment tool in accordance with claim 1, wherein said guide member comprises a graduated scale defined along an outer surface of said guide member.

8. An inspection system for inspecting a condition of a ring gear of a gearbox, the ring gear including an outer surface and a plurality of gear teeth extending radially inwardly from the outer surface, said inspection system comprising:
   a monitoring device for monitoring a condition of the ring gear;
   a transducer coupled to said monitoring device, said transducer positioned adjacent the ring gear outer surface and configured to generate a signal indicative of a defect defined within the ring gear; and,
   an alignment tool removably coupled to the ring gear outer surface, said alignment tool comprising a guide edge oriented substantially parallel to a centerline axis of a predefined ring gear tooth and oriented parallel to and contacting the outer surface, wherein said transducer contacts said guide edge and travels along said guide edge to scan along a length of the ring gear tooth.

9. An inspection system in accordance with claim 8, wherein said alignment tool comprises:
   a support member extending between a leading edge and a trailing edge, said support member removably mountable to the ring gear outer surface such that the leading edge is oriented substantially parallel to a forward surface of the ring gear; and,
   a guide member extending outwardly from said support member, said guide member comprising said guide edge oriented substantially parallel to the gear tooth centerline axis.

10. An inspection system in accordance with claim 9, wherein said alignment tool further comprises a plurality of support magnets coupled to said support member for removably coupling said alignment tool to the ring gear outer surface.

11. An inspection system in accordance with claim 10, wherein said alignment tool further comprises a plurality of alignment magnets positioned adjacent said leading edge, said plurality of alignment magnets spaced along said leading edge to facilitate orienting said leading edge substantially parallel to the ring gear forward surface.

12. An inspection system in accordance with claim 9, wherein said guide member comprises a spacing plate extending outwardly from said support member trailing edge, said spacing plate extends between said guide edge and an opposite rear edge.

13. An inspection system in accordance with claim 12, wherein said spacing plate includes a width measured between said guide edge and said rear edge that is approximately equal to a distance measured between adjacent ring gear teeth.

14. An inspection system in accordance with claim 13, wherein said rear edge is oriented substantially parallel to said guide edge, said guide edge oriented with respect to a first gear tooth and said rear edge oriented with respect to a second gear tooth adjacent the first gear tooth.

15. An inspection system in accordance with claim 9, wherein said guide member comprises a graduated scale defined along an outer surface of the guide member, said graduated scale extending a length that is approximately equal to a length of a ring gear tooth.

16. A method of inspecting a gearbox including a ring gear having a plurality of gear teeth extending radially inwardly from an outer surface, said method comprising:
   removably coupling an alignment tool to the ring gear, the alignment tool including a support member extending between a leading edge and a trailing edge, and a guide member extending outwardly from the support member, the guide member including a guide edge oriented obliquely to the leading edge;
   positioning the alignment tool with respect to a first gear tooth such that the guide edge is oriented with respect to a centerline axis of the first ring gear tooth;
   positioning a transducer adjacent the guide edge;
   transmitting, from the transducer to a monitoring device, a first signal indicative of the first ring gear tooth;
   determining, by the monitoring device, a location of a defect within the first ring gear tooth based at least in part on the received first signal;
   positioning the alignment tool with respect to a second ring gear tooth that is different from the first ring gear tooth such that the guide edge is oriented with respect to a centerline axis of the second ring gear tooth;
   positioning the transducer adjacent the guide edge such that the transducer is oriented with respect to the second ring gear tooth; and,
   transmitting, from the transducer to the monitoring device, a second signal indicative of the second ring gear tooth.

17. A method in accordance with claim 16, further comprising presenting, by the monitoring device, a graphical representation of the first ring gear tooth corresponding to the received first monitoring signal.

18. A method in accordance with claim 16, wherein the ring gear includes a forward surface and an opposite aft surface, said method further comprises positioning the alignment tool leading edge adjacent the forward surface.

* * * * *